US011141469B2

(12) United States Patent
Wyss-Coray et al.

(10) Patent No.: US 11,141,469 B2
(45) Date of Patent: *Oct. 12, 2021

(54) METHODS AND COMPOSITIONS FOR TREATING AGING-ASSOCIATED CONDITIONS

(71) Applicants: THE BOARD OF TRUSTEES OF THE LELAND STANFORD JUNIOR UNIVERSITY, Stanford, CA (US); U.S. GOVERNMENT AS REPRESENTED BY THE DEPARTMENT OF VETERANS AFFAIRS, Washington, DC (US)

(72) Inventors: Anton Wyss-Coray, Palo Alto, CA (US); Joseph M. Castellano, Tuckahoe, NY (US)

(73) Assignees: THE BOARD OF TRUSTEES OF THE LELAND STANFORD JUNIOR UNIVERSITY, Stanford, CA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,073

(22) Filed: Apr. 7, 2020

(65) Prior Publication Data
US 2020/0254075 A1 Aug. 13, 2020

Related U.S. Application Data

(63) Continuation of application No. 15/736,583, filed as application No. PCT/US2016/036032 on Jun. 16, 2016, now Pat. No. 10,617,744.

(60) Provisional application No. 62/175,981, filed on Jun. 15, 2015.

(51) Int. Cl.
*A61K 38/55* (2006.01)
*A61P 25/28* (2006.01)

(52) U.S. Cl.
CPC .............. *A61K 38/55* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 4,872,983 A | 10/1989 | Diamantoglou et al. | |
| 5,240,614 A | 8/1993 | Ofsthun et al. | |
| 5,916,202 A | 6/1999 | Haswell | |
| 6,416,487 B1 | 7/2002 | Braverman et al. | |
| 6,419,830 B2 | 7/2002 | Strom et al. | |
| 6,423,024 B1 | 7/2002 | Strom et al. | |
| 6,475,161 B2 | 11/2002 | Teicher et al. | |
| 6,632,174 B1 | 10/2003 | Breznitz | |
| 6,855,121 B1 | 2/2005 | Chan et al. | |
| 6,946,546 B2 | 9/2005 | Vaughan et al. | |
| 7,196,162 B2 | 3/2007 | Quirk et al. | |
| 7,368,542 B2 | 5/2008 | McIntyre | |
| 7,608,406 B2 | 10/2009 | Valkirs et al. | |
| 7,739,056 B2 | 6/2010 | Landfield et al. | |
| 7,785,601 B2 | 8/2010 | Schaebitz et al. | |
| 7,851,172 B2 | 12/2010 | Lovell et al. | |
| 7,908,090 B2 | 3/2011 | Kim et al. | |
| 8,211,310 B2 | 7/2012 | Young et al. | |
| 8,257,922 B2 | 9/2012 | Liew et al. | |
| 8,272,518 B2 | 9/2012 | Fujita et al. | |
| 8,349,550 B2 | 1/2013 | Brady et al. | |
| 8,772,042 B2 | 7/2014 | Yalkinoglu et al. | |
| 8,778,616 B2 | 7/2014 | Ambati et al. | |
| 8,828,977 B2 | 9/2014 | Zahos et al. | |
| 9,161,968 B2 | 10/2015 | Wyss-Coray et al. | |
| 9,511,094 B2 | 12/2016 | Fraser et al. | |
| 9,770,486 B2 | 9/2017 | Wyss-Coray et al. | |
| 9,782,457 B2 | 10/2017 | Chandler et al. | |
| 2002/0055158 A1* | 5/2002 | Greene | C07K 14/8146 435/184 |
| 2002/0143283 A1 | 10/2002 | Braverman et al. | |
| 2002/0151064 A1 | 10/2002 | Rothenberg et al. | |
| 2003/0139332 A1 | 7/2003 | Noble et al. | |
| 2003/0157687 A1 | 8/2003 | Greene et al. | |
| 2004/0120937 A1 | 6/2004 | Wilson | |

(Continued)

FOREIGN PATENT DOCUMENTS

EP   0184040 61   4/1993
EP   2341138 A1   7/2011

(Continued)

OTHER PUBLICATIONS

Aarsland et al., "Neuropsychiatric symptoms in Parkinson's disease." Mov Disord. Nov. 15, 2009;24(15):2175-86.
Adachi et al., "Intravascular lymphomatosis: a case report" No Shinkei Geka. Jul. 2001;29(7):659-65. Original in Japanese (English abstract obtained from pubmed).
Adair et al., "Measurement of gelatinase B (MMP-9) in the cerebrospinal fluid of patients with vascular dementia and Alzheimer disease." Stroke. Jun. 2004;35(6):e159-62.
Adkins et al. "Toward a human blood serum proteome: analysis by multidimensional separation coupled with mass spectrometry." Mol Cell Proteomics. Dec. 2002;1(12):947-55.

(Continued)

*Primary Examiner* — Adam Weidner
(74) *Attorney, Agent, or Firm* — Casimir Jones, S.C.; Tanya A. Arenson

(57) ABSTRACT

Methods of treating an adult mammal for an aging-associated condition are provided. Aspects of the methods include enhancing a TIMP activity, e.g., a TIMP2 activity, in the mammal in a manner sufficient to treat the adult mammal for the aging-associated condition. Also provided are compositions for use in practicing methods of the invention. A variety of aging-associated conditions may be treated by practice of the methods, which conditions include cognitive impairments.

19 Claims, 1 Drawing Sheet
Specification includes a Sequence Listing.

(56) References Cited

U.S. PATENT DOCUMENTS

| | | |
|---|---|---|
| 2004/0127445 A1 | 7/2004 | Liew et al. |
| 2004/0141946 A1 | 7/2004 | Schaebitz et al. |
| 2004/0254152 A1 | 12/2004 | Monje et al. |
| 2005/0142101 A1 | 6/2005 | Forssmann et al. |
| 2005/0221348 A1 | 10/2005 | Ray et al. |
| 2005/0244448 A1 | 11/2005 | Chen et al. |
| 2006/0031951 A1 | 2/2006 | Klimanskaya et al. |
| 2006/0094064 A1 | 5/2006 | Ray et al. |
| 2006/0198851 A1 | 9/2006 | Basi et al. |
| 2006/0263759 A1 | 11/2006 | Alves-Filho et al. |
| 2007/0037200 A1 | 2/2007 | Ray et al. |
| 2007/0155725 A1 | 7/2007 | Li et al. |
| 2007/0190055 A1 | 8/2007 | Ambati |
| 2008/0026485 A1 | 1/2008 | Hueber et al. |
| 2008/0057590 A1 | 3/2008 | Urdea et al. |
| 2008/0125354 A1 | 5/2008 | Fields et al. |
| 2009/0143394 A1 | 6/2009 | Wyss-Coray et al. |
| 2009/0181008 A1 | 7/2009 | Ray et al. |
| 2009/0209615 A1 | 8/2009 | Lipton et al. |
| 2009/0227673 A1 | 9/2009 | Zhu |
| 2009/0239241 A1 | 9/2009 | Ray et al. |
| 2010/0015235 A1 | 1/2010 | Watson et al. |
| 2010/0080850 A1 | 4/2010 | Hubbel et al. |
| 2010/0119496 A1 | 5/2010 | Wilkison et al. |
| 2010/0124756 A1 | 5/2010 | Ray et al. |
| 2010/0258496 A1 | 10/2010 | Hidaka et al. |
| 2010/0310609 A1 | 12/2010 | Watson et al. |
| 2010/0324079 A1 | 12/2010 | Ohyagi |
| 2011/0117100 A1 | 5/2011 | Britschgi et al. |
| 2011/0142848 A1 | 6/2011 | Chung et al. |
| 2011/0202284 A1 | 8/2011 | McReynolds et al. |
| 2011/0212854 A1 | 9/2011 | Ray et al. |
| 2011/0243947 A1 | 10/2011 | Doody et al. |
| 2012/0095000 A1 | 4/2012 | Wyss-Coray et al. |
| 2012/0230941 A1 | 9/2012 | Sing et al. |
| 2013/0040844 A1 | 2/2013 | Wyss-Coray et al. |
| 2013/0302322 A1 | 11/2013 | Wong et al. |
| 2014/0011689 A1 | 1/2014 | Sandip et al. |
| 2014/0121438 A1 | 5/2014 | Long et al. |
| 2014/0255424 A1 | 9/2014 | Wyss-Coray et al. |
| 2014/0294724 A1 | 10/2014 | Chain et al. |
| 2015/0031562 A1 | 1/2015 | Kantor et al. |
| 2015/0079045 A1 | 3/2015 | Kong |
| 2015/0157664 A1 | 6/2015 | Wyss-Coray et al. |
| 2016/0208011 A1 | 7/2016 | Wyss-Coray et al. |
| 2017/0081415 A1 | 3/2017 | Wong et al. |
| 2017/0232118 A1 | 8/2017 | Wyss-Coray et al. |

FOREIGN PATENT DOCUMENTS

| | | |
|---|---|---|
| JP | 2001-501606 | 9/1997 |
| JP | 2000-290294 | 10/2020 |
| RU | 2428997 C1 | 9/2011 |
| RU | 2470677 C1 | 12/2012 |
| UA | 35656 C2 | 4/2001 |
| WO | WO 1987001597 | 3/1987 |
| WO | WO 1990011287 | 10/1990 |
| WO | WO 1997038314 | 10/1997 |
| WO | WO 1999006098 | 2/1999 |
| WO | WO 2000062836 | 10/2000 |
| WO | WO 2002006480 A2 | 1/2002 |
| WO | WO 2003006006 | 1/2003 |
| WO | WO 2003020403 | 3/2003 |
| WO | WO 2004019043 | 3/2004 |
| WO | WO 2004060425 | 7/2004 |
| WO | WO 2005052592 A2 | 6/2005 |
| WO | WO 2005106492 A2 | 11/2005 |
| WO | WO 2006102170 A2 | 9/2006 |
| WO | WO 2006133423 A1 | 12/2006 |
| WO | WO 2007059135 A2 | 5/2007 |
| WO | WO 2008014314 | 1/2008 |
| WO | WO 2008146018 | 12/2008 |
| WO | WO 2009023814 A2 | 2/2009 |
| WO | WO 2009055729 A1 | 4/2009 |
| WO | WO 2010017443 | 2/2010 |
| WO | WO 2010041617 | 4/2010 |
| WO | WO 2011094535 A2 | 8/2011 |
| WO | WO 2013142135 A1 | 9/2013 |
| WO | WO 2014147095 A1 | 9/2014 |
| WO | WO 2015081166 A1 | 6/2015 |
| WO | WO 2015088915 A1 | 6/2015 |
| WO | WO 2015161112 A1 | 10/2015 |
| WO | WO 2016187217 A2 | 11/2016 |
| WO | WO 2016205004 A2 | 12/2016 |
| WO | WO 2017120461 A1 | 7/2017 |

OTHER PUBLICATIONS

Allodi "modeling motor neuron resilience in ALS using stem cells" accessed from biorxiv (Year: 2018), 28 pages.

Ameer et al., "A novel immunoadsorption device for removing beta2-microglobulin from whole blood." Kidney Int. Apr. 2001;59(4):1544-50.

Anderson et al., "High resolution two-dimensional electrophoresis of human plasma proteins." Proc Natl Acad Sci U S A. Dec. 1977;74(12):5421-5.

Anderson et al., "The human plasma proteome: history, character, and diagnostic prospects." Mol Cell Proteomics. Nov. 2002;1(11):845-67.

Archibald et al., "The retina in Parkinson's disease." Brain. May 2009;132(Pt 5):1128-45.

Astor et al., "Serum β2-microglobulin at discharge predicts mortality and graft loss following kidney transplantation." Kidney Int. Oct. 2013;84(4):810-7.

Baba et al., "Timp-3 deficiency impairs cognitive function in mice." Lab Invest. Dec. 2009;89(12):1340-7.

Baijens et al. "Effects of therapy for dysphagia in Parkinson's disease: systematic review." Dysphagia. Mar. 2009;24(1):91-102.

Berezovskaya et al., "Colony stimulating factor-1 potentiates neuronal survival in cerebral cortex ischemic lesion." Acta Neuropathol. Nov. 1996;92(5):479-86.

Bhattacharya "Placental umbilical cord whole blood transfusion: a safe and genuine blood substitute for patients of the under-resourced world at emergency." J Am Coll Surg. 2005. Submitted 34 pages.

Bhattacharya "Study of the utility of placental cord blood in meeting the transfusion needs of beta-thalassaemic patients" Regional Health Forum, 2008. pp. 16-27.

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.

Borlongan et al., "Central nervous system entry of peripherally injected umbilical cord blood cells is not required for neuroprotection in stroke." Stroke. Oct. 2004;35(10):2385-9.

Bouchard et al. "Aging and brain rejuvenation as systemic events", J. Neurochem. Jan. 2015; 132(1):5-19.

Brehm et al., "Human allograft rejection in humanized mice: a historical perspective." Cell Mol Immunol. May 2012;9(3):225-31.

Brew et al., "The tissue inhibitors of metalloproteinases: An ancient family with structural and functional diversity," Biochimica et Biophysica Acta (2010) 1803: 55-71).

Britschgi et al., "Blood protein signature for the early diagnosis of Alzheimer disease." Arch Neurol. Feb. 2009;66(2):161-5.

Cairo CW et al., Drug-Receptor Interactions, Principles of Pharmacology, (2nd ed.), Chapter 1, pp. 3-18 (2008)).

Cheung et al., "Serum β-2 microglobulin predicts mortality in people with diabetes." Eur J Endocrinol. May 17, 2013;169(1):1-7.

Conboy et al., "Heterochronic parabiosis for the study of the effects of aging on stem cells and their niches." Cell Cycle. Jun. 15, 2012;11(12):2260-7.

Conboy et al., "Heterochronic parabiosis: historical perspective and methodological considerations for studies of aging and longevity." Aging Cell. Jun. 2012;12(3):525-30.

Conboy et al., "Rejuvenation of aged progenitor cells by exposure to a young systemic environment." Nature. Feb. 17, 2005;433(7027). 760-4.

Corbeau et al., "An early postinfection signal mediated by monoclonal anti-beta 2 microglobulin antibody is responsible for delayed

(56) References Cited

OTHER PUBLICATIONS production of human immunodeficiency virus type 1 in peripheral blood mononuclear cells." J Virol. Apr. 1990;64(4):1459-64.

Fedoroff e al., "Role of colony stimulating factor-1 in brain damage caused by ischemic." Neurosci Biobehav Rev. Mar. 1997;21(2):187-91.

Garner "The significance of meaning: why do over 90% of behavioral neuroscience results fail to translate to humans, and what can we do to fix it?" ILAR J. 2014;55(3):438-56.

GHR "Parkinson's disease" accessed from ghr.nlm.nih.gov on Mar. 15, 2019 (Year: 2019), 10 pages.

Gilbert et al., "The Role of Inflammation in Parkinson's Disease" Jun. 12, 2018. Accessed from apdaparkinson.org on Nov. 5, 2019. 11 pages.

Giorgetti et al., "beta2-Microglobulin is potentially neurotoxic, but the blood brain barrier is likely to protect the brain from its toxicity." Nephrol Dial Transplant. Apr. 2009;24(4):1176-81.

Giorgetti et al., "Effect of tetracyclines on the dynamics of formation and destructuration of beta2-microglobulin amyloid fibrils." J Biol Chem. Jan. 21, 2011;286(3):2121-31.

Gomez, et al., "Tissue inhibitors of metalloproteinases: structure, regulation and biological functions," European Journal of Cell Biology (1997) 74: 111-22).

Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.

Jankovic et al., "Current approaches to the treatment of Parkinson's disease." Neuropsychiatr Dis Treat. Aug. 2008;4(4):743-57.

Jha, Alok. "Young blood can reverse some effects of ageing, study finds", The Guardian, Oct. 17, 2012, 4 pages.

Kassiri, et al., "Tissue inhibitor of metalloproteinases (TIMPs) in heart failure," Heart Failure Reviews (2012) 17: 693-706).

Katcher "Studies that shed new light on aging." Biochemistry (Mosc). Sep. 2013;78(9):1061-70.

Kegel "Inflammatory Processes in Huntington's: Researchers Seek to Understand Influence on Disease" accessed from huntingtonsdiseasenews.com on Nov. 5, 2019. (year: 2016) 10 pages.

Kempermann et al., "Genetic determinants of adult hippocampal neurogenesis correlate with acquisition, but not probe trial performance, in the water maze task." Eur J Neurosci. Jul. 2002;16(1):129-36.

Komosinkska-Vassev, et al., "Age-and gender-dependent changes in connective tissue remodeling: physiological differences in circulating MMP-3, MMP-10, TIMP-1, and TIMP-2 levels," Gerontology (2011) 57: 44-52).

Krementsov "A Martian Stranded on Earth: Alexander Bogdanov, Blood Transfusions, and Proletarian Science" pp. 57-59,85,86, and 88. University of Chicago Press, Chicago, United States, 2011.

Kwak et al., "Aging, exercise, and extracellular matrix in the heart." J Exerc Rehabil. Jun. 30, 2013;9(3):338-47.

Lees et al., "Parkinson's disease" Lancet. Jun 30, 2013;373(9680):2055-66.

Lee, et al., "Effects of aging on blood brain barrier and matrix metalloproteases following controlled cortical impact in mice," Experimental Neurology (2012) 234: 50-61).

Lin et al., "Discovery of a cytokine and its receptor by functional screening of the extracellular proteome." Science. May 9, 2008;320(5877):807-11.

Loffredo et al., "Growth differentiation factor 11 is a circulating factor that reverses age-related cardiac hypertrophy." Cell. May 9 2013;153(4):828-39.

Longo "Alzheimer's Prevention, Treatment and Research-A Q&A" Stanford Health Now, 2016, 1-2.

Luo et al. "Colony-stimulating factor 1 receptor (CSF1R) signaling in injured neurons facilitates protection and survival.", J. Exp. Med. (2013) 210(1):157-172.

Lysaght et al., "Beta-2 microglobulin removal during continuous ambulatory peritoneal dialysis (CAPD)." Perit Dial Int. 1989;9(1):29-35.

Malkki, H. "Ageing: Could young blood combat age-related cognitive decline?" Nat. Rev. Neurol. Jun. 2014;10(6):307.

Manzo et al., "Role of chemokines and chemokine receptors in regulating specific leukocyte trafficking in the immune/inflammatory response." Clin Exp Rheumatol. Jul.-Aug. 2003;21(4):501-8.

Perez-Martinez et al. "Tissue inhibitor of metalloproteinase-2 promotes neuronal differentiation by acting as an anti-mitogenic signal." J Neurosci. May 18, 2005;25(20):4917-29.

Martino et al., "Circulating MicroRNAs Are Not Eliminated by Hemodialysis" (2012) Circulating MicroRNAs Are Not Eliminated by Hemodialysis. PLOS ONE 7(6): e38269.

Mayer et al., "Identification of receptor binding and activation determinants in the N-terminal and N-loop regions of the CC chemokine eotaxin."J Biol Chem. Apr. 21, 2001;276(17):13911-6.

Mebane-Sims (2009). Alzheimer's Disease Facts and Figures. Alzheimer's & Dementia. 5. 234-270. 10.1016/j.jalz.2009.03.001.

McLaurin et al., "Microglial pilgrimage to the brain." Nat Med. Dec. 2010;16(12):1380-1.

Middeldorp et al. "A young systemic environment reverses degeneration in a mouse model of Alzheimer's disease", Neuroscience 2012, Presentation Abstract, Oct. 16, 2012, 2 pages.

Mitrasinovic et al., "Microglia overexpressing the macrophage colony-stimulating factor receptor are neuroprotective in a microglial-hippocampal organotypic coculture system." J Neurosci. Apr. 27, 2005;25(17):4442-51.

Mizuno e al., "Interleukin-34 selectively enhances the neuroprotective effects of microglia to attenuate oligomeric amyloid-β neurotoxicity." Am J Pathol. Oct. 2011;179(4):2016-27.

Moore et al., "An Alternate Perspective on the Roles of TIMPs and MMPs in Pathology," The American Journal of Pathology (2012) 180: 12-16).

Morais et al., "High molecular weight plasma proteins induce apoptosis and Fas/FasL expression in human proximal tubular cells." Nephrol Dial Transplant. Jan. 2005;20(1):50-8.

Morton e al., "Establishment of human tumor xenografts in immunodeficient mice." Nat Protoc. 2007;2(2):247-50.

Murphy, "Tissue inhibitors of metalloproteinases," Genome Biology (2011) 12).

Niezgoda et al., "The effect of cladribine treatment on beta-2 microglobin in the cerebrospinal fluid and serum of patients with multiple sclerosis" Neurol Neurochir Pol. Mar.-Apr. 2000;34(2):281-7. (Abstract).

Nomura et al. "Basic concept of development and practical application of animal models for human diseases." Curr Top Microbiol Immunol. 2008;324:1-24.

Palop et al., "A network dysfunction perspective on neurodegenerative diseases." Nature. Oct. 19, 2006;443(7113):768-73.

Pearson et al. "Humanized SCID mouse models for biomedical research." Curr Top Microbiol Immunol. 2008;324:25-51.

Politis et al., "Parkinson's disease symptoms: the patient's perspective." Mov Disord. Aug. 15, 2010;25(11):1646-51.

Prakasam et al., "Amyloid and Neurodegeneration: Alzheimer's Disease and Retinal Degeneration" Chapter 7, Handbook of Neurochemistry and Molecular Neurobiology, Lajtha ed., 2009, 131-163. (Year: 2009).

Reitz, "Toward precision medicine in Alzheimer's disease." Ann Transl Med. Mar. 2016;4(6):107.

Ron-Harel et al. "Age-Dependent Spatial Memory Loss Can Be Partially Restored by Immune Activation", Rejuvenation Resarch (2008), 11(5):903-13.

Royer et al., "A novel antagonist of prostaglandin 02 blocks the locomotion of eosinophils and basophils." Eur J Clin nvesl. Sep. 2008;38(9):663-71.

Schwartz et al. "How Do Immune Cells Support and Shape the Brain in Health, Disease, and Aging?" The Journal of Neuroscience, Nov. 6, 2013, 33(45):17587-96.

(56) References Cited

OTHER PUBLICATIONS

Sellebjerg, et al., "Identification of new sensitive biomarkers for the in vivo response to interferon-beta treatment in multiple sclerosis using DNA-array evaluation." Eur J Neurol. Dec. 2009;16(12):1291-8.
Shen et al., "CCR3 monoclonal antibody inhibits airway eosinophilic inflammation and mucus overproduction in a mouse model of asthma." Acta Pharmacol Sin. Dec. 2009;27(12):1594-9.
Shin et al., "Association of Eotaxin gene family with asthma and serum total IgE." Hum Mol Genet. Jun. 1, 2003;12(11):1279-85.
Simonsen et al., "Novel panel of cerebrospinal fluid biomarkers for the prediction of progression to Alzheimer dementia in patients with mild cognitive impairment." Arch Neurol. Mar. 2007;64(3):366-70.
Skovronsky et al., "Neurodegenerative diseases: new concepts of pathogenesis and their therapeutic implications." Annu Rev Pathol. 2006;1:151-70.
Smith et al., "β-microglobulin is a systemic pro-aging factor that impairs cognitive function and neurogenesis." Nat Med. Aug. 2015;21(8):932-7.
Stetler-Sstevenson et al., "TIMP-2: an endogenous inhibitor of angiogenesis," Trends in Molecular Medicine (2005) 11: 97-103).
Stetler-Stevenson, "Tissue Inhibitors of Metalloproteinases in Cell Signaling," Science Signaling (2008) 1).
Strobel et al., "Chicago: The Vampire Principle—Young Blood Rejuvenates Aging Brain?", Alzheimer Research Forum (Nov. 2009), p. 1-3.
Stubbs et al., "Indomethacin causes prostaglandin 0(2)-like and eotaxin-like selective responses in eosinophils and basophils." J Biol Chem. Jul. 19, 2002;277(29):26012-20.
Suzuki et al., "Beta2-microglobulin-selective adsorbent column (Lixelle) for the treatment of dialysis-related amyloidosis." Ther Apher Dial. Feb. 2003;7(1):104-7.
Takeda et al., "CCR3 is a target for age-related macular degeneration diagnosis and therapy." Nature. Jul. 9, 2009;460(7252):225-30.
Teixeira, A.L. et al, "Increased serum levels of CCL 11/eotaxin in schizophrenia", Process in Neuro-Psychopharmacology & Biological Psychiatry, vol. 32, No. 3, pp. 710-714, 2008.
Thomson et al. "Young blood for a keener mind", NewScientist (2012), 216(2887):10.
Villeda et al. "The aging systemic milieu negatively regulates neurogenesis and cognitive function", Nature, Aug. 31, 2011, 477(7362):90-4.
Villeda et al. "Young blood reverses age-related cognitive impairments", Neuroscience 2012, Presentation Abstract, Oct. 17, 2012, 2 pages.
Villeda et al. "Young blood reverses age-related impairments in cognitive function and synaptic plasticity in mice", Nat Med. (Jun. 2014), 20(6):659-63.
Villeda et al., "Changes in the systemic milieu modulate neurogenesis during aging" Abstract, 39th Annual Neuroscience Meeting, Chicago, IL, Society for Neuroscience, Oct. 2009, 1-2. (Year: 2009).
Villeda et al., Meeting Date, Past and Future Meetings, 39th Annual Neuroscience Meeting, Society for Neuroscience, 2009, 1. (Year: 2009).
Vincent et al., "Macrophage colony stimulating factor prevents NMDA-induced neuronal death in hippocampal organotypic cultures." J Neurochem. Sep. 2002;82(6):1388-97.
Visse et al. "Matrix Metalloproteinases and Tissue Inhibitors of Metalloproteinases," Circulation Research (2003) 92: 827-39).
Wang et al., "Expression of colony stimulating factor-1 receptor (CSF-1R) by CNS neurons in mice." J Neurosci Res. Sep. 1, 1999;57(5):616-32.
Wang et al., "Upregulation of CCR3 by age-related stresses promotes choroidal endothelial cell migration via VEGF-dependent and -independent signaling." Invest Ophthalmol Vis Sci. Oct. 21, 2011;52(11):8271-7.
Wang et al., "Matrix metalloproteinases and their multiple roles in Alzheimer's disease." Biomed Res Int. 2014;2014:908636.
Website document entitled "Plasma Protein Composition" (available at http://www.sigmaaldrich science/metabolomics/enzyme-explorer/learning-center/plasma-blood-proteins/plasma-protein-composition.html). Downloaded from internet Jun. 27, 2017., 3 pages.
Wikipedia A "Huntingtin" accessed on Mar. 15, 2019 (excerpt) (Year: 2019).
Wikipedia B "Huntington's disease (Genetics)" accessed Mar. 15, 2019 (excerpt) (Year: 2019).
Wilson et al., "Beta2-microglobulin as a biomarker in peripheral arterial disease: proteomic profiling and clinical studies." Circulation. Sep. 18, 2007;116(12):1396-403.
Xu, et al., "Matrix Metalloproteinase Inhibitors: A review on Bioanalytical Methods, Pharmacokinetics and Metabolism," Current Drug Metabolism (2011) 12: 395-410).
Yagihashi A. et al., "Macrophage colony stimulating factor (M-CSF) protects spiral ganglion neurons following auditory nerve injury: morphological and functional evidence." Exp Neurol. Mar. 2005;192(1):167-77.
Yamane et al., "CSF-1 receptor-mediated differentiation of a new type of monocytic cell with B cell-stimulating activity: its selective dependence on IL-34." J Leukoc Biol. Jan. 2014;95(1):19-31.
Ye, et al., "Haptoglobin-alpha subunit as potential serum biomarker in ovarian cancer: identification and characterization using proteomic profiling and mass spectrometry." Clinical Cancer Research (Aug. 2003), 9 (8):2904-11.
SFN "Young blood can reverse some effects of ageing, study finds", Author Unknown, Society for Neuroscience, The Observer, Oct. 24, 2012, 2 pages, Retrieved online: http://gonzoj.wordpress.com/tag/society-for-neuroscience/.
Zheng et al., "Agonist-selective signaling of G protein-coupled receptor: mechanisms and implications." IUBMB Life. Feb. 2010;62(2):112-9.
Search Report dated Aug. 2, 2017, for related European application No. 14868769.2, 8 pages.
Search Report of related PCT/US2011/022916, dated Oct. 31, 2011, 11 pages.
Search Report of related PCT/US2014/068897, dated Feb. 27, 2015, 11 pages.
Search Report of related PCT/US2016/032907, dated Dec. 1, 2016, 24 pages.
Search Report of related PCT/US2016/036032, dated Feb. 21, 2017, 13 pages.
Search Report of related PCT/US2017/012521, dated Feb. 2, 2017, 12 pages.
Examiner Report of 2016265948, dated May 11, 2018, 6 pages.
Examiner Report of 738184, dated Apr. 6, 2018, 4 pages.
Examiner Report of 720949, dated Jan. 18, 2019, 5 pages.
Examiner Report of 2014364182, 4 pages, dated Jan. 17, 2019.
Ashabi, G. et al. Time course study of Ab formation and neurite outgrowth disruption in differentiated human neuroblastoma cells exposed to H202: Protective role of autophagy. Toxicol In Vitro. Sep. 2013;27(6): 1780-8.
Brew, K. et al. The tissue inhibitors of metalloproteinases (TIMPs): An ancient family with structural and functional diversity. Biochim Biophys Acta. Jan. 2010;1803(1):55-71.
Khodagholi, F. et al. 3-Thiomethyl-5, 6-(dimethoxyphenyl)-1,2, 4-triazine improves neurite outgrowth and modulates MAPK, phosphorylation and HSPs expression in H2O2-exposed PC12 cells. Toxicol In Vitro. Sep. 2012;26(6):907-14.
Perez-Martinez, Leonor et al. "Tissue Inhibitor of Metalloproteinase-2 promotes neuronal differentiation by acting as an anti-mitogenic signal: TIMP-2 mediated differentiation is MMP-independent", The Journal of neuroscience : the official journal of the Society for Neuroscience, May 18, 2005 (May 18, 2005), pp. 4917-4929, XP055528323, DOI: 10.1523/JNEUROSCI.5066-04. 2005 Retrieved from the Internet: URL:https://www.ncbi.nlm.nih. gov/pmc/articles/PMC1282460/pdf/nihms2652.pdf.
"TIMP metallopeptidase inhibitor 4 [*Homo sapiens*]", Venter, J.C., et al., GenBank, Accession No. EAW64122.1.
"TIMP1 [*Homo sapiens*]", Halleck, A., GenBank, Accession No. CAG46779.1.
"TIMP2, partial [synthetic construct]", Sahni, N., GenBank, Accession No. AK171693.1.

(56) References Cited

OTHER PUBLICATIONS

"TIMP3 [*Homo sapiens*]", Collins, J. E., GenBank, Accession No. CAG30479.1.

* cited by examiner

METHODS AND COMPOSITIONS FOR TREATING AGING-ASSOCIATED CONDITIONS

CROSS-REFERENCE TO RELATED APPLICATIONS

This application is continuation of U.S. patent application Ser. No. 15/736,583, filed Dec. 14, 2017, now U.S. Pat. No. 10,617,744, issued Apr. 14, 2020, which is a U.S. 371 national phase entry of International Patent Application No. PCT/US2016/036032, filed Jun. 6, 2016, which claims priority to the filing date of the U.S. Provisional Patent Application Ser. No. 62/175,981 filed Jun. 15, 2015, the disclosure of which applications are incorporated herein by reference in their entireties.

GOVERNMENT RIGHTS

This invention was made with Government support under contract AG045034 awarded by the National Institutes of Health. The Government has certain rights in the invention.

INTRODUCTION

Aging in an organism is accompanied by an accumulation of changes over time. In the nervous system, aging is accompanied by structural and neurophysiological changes that drive cognitive decline and susceptibility to degenerative disorders in healthy individuals. (Heeden & Gabrieli, "Insights into the ageing mind: a view from cognitive neuroscience," Nat. Rev. Neurosci. (2004) 5: 87-96; Raz et al., "Neuroanatomical correlates of cognitive aging: evidence from structural magnetic resonance imaging," Neuropsychology (1998) 12:95-114; Mattson & Magnus, "Ageing and neuronal vulnerability," Nat. Rev. Neurosci. (2006) 7: 278-294; and Rapp & Heindel, "Memory systems in normal and pathological aging," Curr. Opin. Neurol. (1994) 7:294-298). Included in these changes are synapse loss and the loss of neuronal function that results. Thus, although significant neuronal death is typically not observed during the natural aging process, neurons in the aging brain are vulnerable to sub-lethal age-related alterations in structure, synaptic integrity, and molecular processing at the synapse, all of which impair cognitive function.

In addition to the normal synapse loss during natural aging, synapse loss is an early pathological event common to many neurodegenerative conditions, and is the best correlate to the neuronal and cognitive impairment associated with these conditions. Indeed, aging remains the single most dominant risk factor for dementia-related neurodegenerative diseases such as Alzheimer's disease (AD) (Bishop et al., "Neural mechanisms of ageing and cognitive decline," Nature (2010) 464: 529-535 (2010); Heeden & Gabrieli, "Insights into the ageing mind: a view from cognitive neuroscience," Nat. Rev. Neurosci. (2004) 5:87-96; Mattson & Magnus, "Ageing and neuronal vulnerability," Nat. Rev. Neurosci. (2006) 7:278-294).

As the human lifespan increases, a greater fraction of the population suffers from aging-associated cognitive impairments, making it crucial to elucidate means by which to maintain cognitive integrity by protecting against, or even counteracting, the effects of aging (Hebert et al., "Alzheimer disease in the US population: prevalence estimates using the 2000 census," Arch. Neurol. (2003) 60:1119-1122; Bishop et al., "Neural mechanisms of ageing and cognitive decline," Nature (2010) 464:529-535).

Tissue inhibitor of metalloproteinase 2 (TIMP-2) is a member of a group of specific inhibitors of matrix metalloproteinases. The proteins these inhibitors regulate, matrix metalloproteinases (MMPs), play a role in several physiological processes including growth, wound healing, tissue repair, and cellular development and homeostasis. Broad categories of MMPs consist of collagenases, gelatinases, stromelysins, matrilysins, membrane-type MMPs (MT-MMPs), and others. These enzymes must be precisely regulated as the loss of control over MMP activity may result in arthritis, cancer, atherosclerosis, aneurysms, nephritis, tissue ulcers, fibrosis, and other tissue damage (Visse and Nagase, "Matrix Metalloproteinases and Tissue Inhibitors of Metalloproteinases," Circulation Research (2003) 92: 827-39). Four TIMPs (1-4) have been identified in vertebrates.

SUMMARY

Methods of treating an adult mammal for an aging-associated condition are provided. Aspects of the methods include enhancing a TIMP activity, e.g., a TIMP2 activity, in the mammal in a manner sufficient to treat the adult mammal for the aging-associated condition. Also provided are compositions for use in practicing methods of the invention. A variety of aging-associated conditions may be treated by practice of the methods, which conditions include cognitive impairments.

DETAILED DESCRIPTION

Figure 1A:
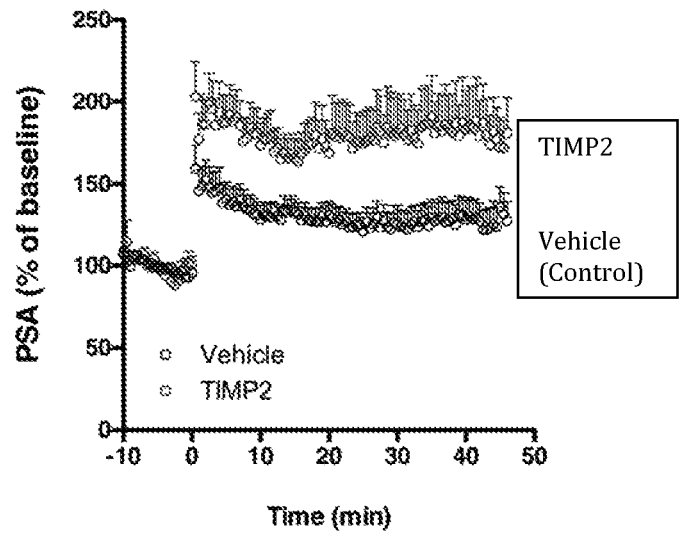
FIG. 1A shows the results on brain slices isolated from aged wildtype mice that were treated with recombinant TIMP2 (i.p., 50 µg/kg)(bottom) or a control (top).

Methods of treating an adult mammal for an aging-associated condition are provided. Aspects of the methods include enhancing TIMP activity, e.g., a TIMP2 activity, in the mammal in a manner sufficient to treat the adult mammal for the aging-associated condition. Also provided are compositions for use in practicing methods of the invention. A variety of aging-associated conditions may be treated by practice of the methods, which conditions include cognitive impairments.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

As summarized above, aspects of the invention include methods of treating an aging-associated condition in an adult mammal. The aging-associated condition may manifest in a number of different ways, e.g., as aging-associated cognitive impairment and/or physiological impairment, e.g., in the form of damage to central or peripheral organs of the body, such as but not limited to: cell injury, tissue damage, organ dysfunction, aging-associated lifespan shortening and carcinogenesis, where specific organs and tissues of interest include, but are not limited to skin, neuron, muscle, pancreas, brain, kidney, lung, stomach, intestine, spleen, heart, adipose tissue, testes, ovary, uterus, liver and bone; in the form of decreased neural plasticity, etc.

In some embodiments, the aging-associated condition is an aging-associated impairment in cognitive ability in an individual, i.e., an aging-associated cognitive impairment. By cognitive ability, or "cognition", it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. Aging-associated cognitive impairments include impairments in cognitive ability that are typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington's disease, amyotrophic lateral sclerosis, multiple sclerosis, glaucoma, muscular dystrophy, vascular dementia, and the like.

By "treatment" it is meant that at least an amelioration of one or more symptoms associated with an aging-associated condition afflicting the adult mammal is achieved, where amelioration is used in a broad sense to refer to at least a reduction in the magnitude of a parameter, e.g., a symptom associated with the impairment being treated. As such, treatment also includes situations where a pathological condition, or at least symptoms associated therewith, are completely inhibited, e.g., prevented from happening, or stopped, e.g., terminated, such that the adult mammal no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased synaptic efficacy, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered prior to the symptomatic state of the disease, during the symptomatic stage of the disease, and in some cases after the symptomatic stage of the disease.

In some instances where the aging-associated condition is aging-associated cognitive decline, treatment by methods of the present disclosure slows, or reduces, the progression of aging-associated cognitive decline. In other words, cognitive abilities in the individual decline more slowly, if at all, following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from aging-associated cognitive decline is halted following treatment by the disclosed methods. As another example, cognitive decline in an individual, e.g., an individual 40 years old or older, that is projected to suffer from aging-associated cognitive decline, is prevented following treatment by the disclosed methods. In other words, no (further) cognitive impairment is observed. In some instances, treatment by methods of the present disclosure reduces, or reverses, cognitive impairment, e.g., as observed by improving cognitive abilities in an individual suffering from aging-associated cognitive decline. In other words, the cognitive abilities of the individual suffering from aging-associated cognitive decline following treatment by the disclosed methods are better than they were prior to treatment by the disclosed methods, i.e., they improve upon treatment. In some instances, treatment by methods of the present disclosure abrogates cognitive impairment. In other words, the cognitive abilities of the individual suffering from aging-associated cognitive decline are restored, e.g., to their level when the individual was about 40 years old or less, following treatment by the disclosed methods, e.g., as evidenced by improved cognitive abilities in an individual suffering from aging-associated cognitive decline.

In some instances, treatment of an adult mammal in accordance with the methods results in a change in a central organ, e.g., a central nervous system organ, such as the brain, spinal cord, etc., where the change may manifest in a number of different ways, e.g., as described in greater detail below, including but not limited to molecular, structural and/or functional, e.g., in the form of enhanced synaptic plasticity. In some instances, treatment of a subject in accordance with the methods results in a change in a peripheral organ, such as liver, muscle, heart, blood, etc., where the change may manifest in a number of different ways, e.g., as described in greater detail below.

As summarized above, methods described herein are methods of treating an aging-associated condition, e.g., as described above, in an adult mammal. By adult mammal is meant a mammal that has reached maturity, i.e., that is fully developed. As such, adult mammals are not juvenile. Mammalian species that may be treated with the present methods include canines and felines; equines; bovines; ovines; etc., and primates, including humans. The subject methods, compositions, and reagents may also be applied to animal models, including small mammals, e.g., murine, lagomorpha, etc., for example, in experimental investigations. The discussion below will focus on the application of the subject methods, compositions, reagents, devices and kits to humans, but it will be understood by the ordinarily skilled artisan that such descriptions can be readily modified to other mammals of interest based on the knowledge in the art.

The age of the adult mammal may vary, depending on the type of mammal that is being treated. Where the adult mammal is a human, the age of the human is generally 18 years or older. In some instances, the adult mammal is an individual suffering from or at risk of suffering from an aging-associated impairment, such as an aging-associated cognitive impairment, where the adult mammal may be one that has been determined, e.g., in the form of receiving a diagnosis, to be suffering from or at risk of suffering from an aging-associated impairment, such as an aging-associated cognitive impairment. The phrase "an individual suffering from or at risk of suffering from an aging-associated cognitive impairment" refers to an individual that is about 50 years old or older, e.g., 60 years old or older, 70 years old or older, 80 years old or older, and sometimes no older than 100 years old, such as 90 years old, i.e., between the ages of about 50 and 100, e.g., 50, 55, 60, 65, 70, 75, 80, 85 or about 90 years old. The individual may suffer from an aging associated condition, e.g., cognitive impairment, associated with the natural aging process, e.g., M.C.I. Alternatively, the individual may be 50 years old or older, e.g., 60 years old or older, 70 years old or older, 80 years old or older, 90 years old or older, and sometimes no older than 100 years old, i.e., between the ages of about 50 and 100, e.g., 50, 55, 60, 65, 70, 75, 80, 85, 90, 95 or about 100 years old, and has not yet begun to show symptoms of an aging associated condition, e.g., cognitive impairment. In yet other embodiments, the individual may be of any age where the individual is suffering from a cognitive impairment due to an aging-associated disease, e.g., Alzheimer's disease, Parkinson's disease, frontotemporal dementia, Huntington's disease, amyotrophic lateral sclerosis, multiple sclerosis, glaucoma, muscular dystrophy, dementia, and the like. In some instances, the individual is an individual of any age that has been diagnosed with an aging-associated disease that is typically accompanied by cognitive impairment, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, muscular dystrophy, dementia, and the like, where the individual has not yet begun to show symptoms of cognitive impairment.

As summarized above, aspects of the methods include enhancing a TIMP activity, e.g., a systemic TIMP activity, in the mammal in a manner sufficient to treat the adult mammal for the aging-associated condition. By enhancing a TIMP activity is meant increasing one or more target TIMP activities in the subject. In some instances, the TIMP activity that is enhanced is a systemic TIMP activity, by which is meant a TIMP activity in the circulatory system of the mammal. The magnitude of the increase may vary, where in some instances the magnitude of the increase is 2-fold or greater, such as 5-fold or greater, including 10-fold or greater, e.g., 15-fold or greater, 20-fold or greater, 25-fold or greater (as compared to a suitable control). The TIMP activity that is increased by practice of the methods is a TIMP mediated process that is beneficial in treating an aging associated condition. In other words, the TIMP activity that is enhanced is one that results in treatment, e.g., as described above, of the subject for the aging associated condition.

The target TIMP activity that is enhanced may vary. In some instances, the target TIMP activity is a TIMP2 activity, i.e., an activity exhibited by a TIMP2 protein. As such, by TIMP2 activity is meant an activity of interest of a TIMP2 protein, i.e., an activity that results in treatment of an aging-associated condition, e.g., as described above. Of interest are mammalian TIMP2 proteins, such as but not limited to: primate, e.g., human, canine, feline, equine, bovine, ovine, murine, lagomorpha, etc. The sequence of human TIMP2 is:

```
                                           (SEQ ID NO: 01)
         10         20         30         40
  MGAAARTLRL ALGLLLLATL LRPADACSCS PVHPQQAFCN 50         60         70         80
  ADVVIRAKAV SEKEVDSGND IYGNPIKRIQ YEIKQIKMFK 90        100        110        120
  GPEKDIEFIY TAPSSAVCGV SLDVGGKKEY LIAGKAEGDG
```

```
            130       140       150       160
       KMHITLCDFI VPWDTLSTTQ KKSLNHRYQM GCECKITRCP 170       180       190       200
       MIPCYISSPD ECLWMDWVTE KNINGHQAKF FACIKRSDGS 210       220
       CAWYRGAAPP KQEFLDIEDP
```

In some instances, the target TIMP activity is a TIMP1 activity, i.e., an activity exhibited by a TIMP1 protein. As such, by TIMP1 activity is meant an activity of interest of a TIMP1 protein, i.e., an activity that results in treatment of an aging-associated condition, e.g., as described above. Of interest are mammalian TIMP1 proteins, such as but not limited to: primate, e.g., human, canine, feline, equine, bovine, ovine, murine, lagomorpha, etc. The sequence of human TIMP1 is:

```
                                         (SEQ ID NO: 02)
            10        20        30        40
       MAPFEPLASG ILLLLWLIAP SRACTCVPPH PQTAFCNSDL 50        60        70        80
       VIRAKFVGTP EVNQTTLYQR YEIKMTKMYK GFQALGDAAD 90       100       110       120
       IRFVYTPAME SVCGYFHRSH NRSEEFLIAG KLQDGLLHIT 130       140       150       160
       TCSFVAPWNS LSLAQRRGFT KTYTVGCEEC TVFPCLSIPC 170       180       190       200
       KLQSGTHCLW TDQLLQGSEK GFQSRHLACL PREPGLCTWQ

SLRSQIA
```

In some instances, the target TIMP activity is a TIMP3 activity, i.e., an activity exhibited by a TIMP3 protein. As such, by TIMP3 activity is meant an activity of interest of a TIMP3 protein, i.e., an activity that results in treatment of an aging-associated condition, e.g., as described above. Of interest are mammalian TIMP3 proteins, such as but not limited to: primate, e.g., human, canine, feline, equine, bovine, ovine, murine, lagomorpha, etc. The sequence of human TIMP3 is:

```
                                         (SEQ ID NO: 03)
            10        20        30        40
       MTPWLGLIVL LGSWSLGDWG AEACTCSPSH PQDAFCNSDI 50        60        70        80
       VIRAKVVGKK LVKEGPFGTL VYTIKQMKMY RGFTKMPHVQ 90       100       110       120
       YIHTEASESL CGLKLEVNKY QYLLTGRVYD GKMYTGLCNF 130       140       150       160
       VERWDQLTLS QRKGLNYRYH LGCNCKIKSC YYLPCFVTSK 170       180       190       200
       NECLWTDMLS NFGYPGYQSK HYACIRQKGG YCSWYRGWAP

210
       PDKSIINATD P
```

In some instances, the target TIMP activity is a TIMP4 activity, i.e., an activity exhibited by a TIMP4 protein. As such, by TIMP2 activity is meant an activity of interest of a TIMP4 protein, i.e., an activity that results in treatment of an aging-associated condition, e.g., as described above. Of interest are mammalian TIMP4 proteins, such as but not limited to: primate, e.g., human, canine, feline, equine, bovine, ovine, murine, lagomorpha, etc. The sequence of human TIMP4 is:

```
                                         (SEQ ID NO: 04)
            10        20        30        40
       MPGSPRPAPS WVLLILLLAL LRPPGLGEAC SCAPAHPQQH 50        60        70        80
       ICHSALVIRA KISSEKVVPA SADPADTEKM LRYEIKQIKM 90       100       110       120
       FKGFEKVKDV QYIYTPFDSS LCGVKLEANS QKQYLLTGQV 130       140       150       160
       LSDGKVFIHL CNYIEPWEDL SLVQRESLNH HYHLNCGCQI 170       180       190       200
       TTCYTVPCTI SAPNECLWTD WLLERKLYGY QAQHYVCMKH 210       220
       VDGTCSWYRG HLPLRKEFVD IVQP
```

The target TIMP activity or activities of interest may be enhanced using any convenient protocol. In some instances, the target TIMP activity is enhanced by increasing a systemic level of a TIMP active agent in the mammal. By systemic level is meant the level (e.g., concentration or amount) of the TIMP active agent in the circulatory system of the mammal. The magnitude of the increase may vary, where in some instances the magnitude of the increase is 2-fold or greater, such as 5-fold or greater, including 10-fold or greater, e.g., 15-fold or greater, 20-fold or greater, 25-fold or greater (as compared to a suitable control).

In these embodiments, the systemic level of the TIMP active agent of interest may be increased using any convenient protocol. In some instances, the systemic level is increased by administering a TIMP active agent to the subject. In such instances, the TIMP active agent may vary. TIMP active agents that may be employed in these embodiments of the invention include TIMP polypeptides and nucleic acids encoding the same.

TIMP polypeptides are polypeptides that, upon administration to a subject, exhibit the desired TIMP aging associated condition treatment activity, e.g., as described above. The term "polypeptide" as used herein refers to full-length proteins as well as portions or fragments thereof which exhibit the desired TIMP activity. Also included in this term are variations of the naturally occurring proteins, where such variations are homologous or substantially similar to the naturally occurring protein, as described in greater detail below, be the naturally occurring protein the human protein, mouse protein, or protein from some other species which naturally expresses a TIMP protein. In the following description, the term TIMP is used to refer not only to the human form of a TIMP protein, but also to homologs thereof expressed in non-human species.

TIMP polypeptides of interest may vary in terms of amino acid sequence length and molecular weight. In some instances, the TIMP polypeptides range in length from 175 to 350, such as from 200 to 250 and including from about 200 to 225 amino acid residues, and have a projected molecular weight based solely on the number of amino acid residues in the protein and assuming an average molecular weight of 110 Daltons that ranges from 19 to 39 kDa, such as 22 to 28 kDa, including 22 to 25 kDa, where the actual molecular weight may vary depending on the amount of glycosylation of the protein and the apparent molecular weight may be considerably less because of SDS binding on gels. TIMP polypeptides as described herein may be obtained from naturally sources, e.g., via purification techniques, chemically synthesized or produced using recombinant protocols, as desired.

In some instances, the TIMP polypeptide that is administered to the subject is a human TIMP2 protein, where the human TIMP2 protein has an amino acid sequence that comprises a region substantially the same as or identical to the sequence appearing as SEQ ID NO:01. By substantially the same as is meant a protein having a region with a sequence that is 60% or greater, such as 75% or greater, such as 90% or greater and including 98% or greater sequence identity with the sequence of SED ID NO:01, as determined by BLAST using default settings. In some instances, the TIMP polypeptide that is administered to the subject is a human TIMP1 protein, where the human TIMP1 protein has an amino acid sequence that comprises a region substantially the same as or identical to the sequence appearing as SEQ ID NO:02. By substantially the same as is meant a protein having a region with a sequence that is 60% or greater, such as 75% or greater, such as 90% or greater and including 98% or greater sequence identity with the sequence of SED ID NO:02, as determined by BLAST using default settings. In some instances, the TIMP polypeptide that is administered to the subject is a human TIMP3 protein, where the human TIMP3 protein has an amino acid sequence that comprises a region substantially the same as or identical to the sequence appearing as SEQ ID NO:03. By substantially the same as is meant a protein having a region with a sequence that is 60% or greater, such as 75% or greater, such as 90% or greater and including 98% or greater sequence identity with the sequence of SED ID NO:03, as determined by BLAST using default settings. In some instances, the TIMP polypeptide that is administered to the subject is a human TIMP4 protein, where the human TIMP4 protein has an amino acid sequence that comprises a region substantially the same as or identical to the sequence appearing as SEQ ID NO:04. By substantially the same as is meant a protein having a region with a sequence that is 60% or greater, such as 75% or greater, such as 90% or greater and including 98% or greater sequence identity with the sequence of SED ID NO:04, as determined by BLAST using default settings.

In addition to the specific TIMP proteins described above, homologs or proteins (or fragments thereof) from other species, e.g., other animal species, may also be employed in embodiments of the methods, where such homologs or proteins may be from a variety of different types of species, including animals, such as mammals, e.g., rodents, such as mice, rats; domestic animals, e.g., horse, cow, dog, cat; etc. By homolog is meant a protein having 35% or more, such as 40% and more and including 60% or more amino acid sequence identity to the specific TIMP proteins as identified in SEQ ID NOS: 01 to 04, where sequence identity is determined using BLAST at default settings.

In addition to the naturally occurring TIMP proteins, e.g., as described above, TIMP polypeptides that vary from the naturally occurring TIMP proteins may also be employed in practicing methods of the invention. Different variations may be present, including but not limited to substitution, insertion and/or deletion mutations, as well as other types of non-amino acid sequence variations, e.g., as illustrated below. TIMP polypeptides that may be employed include proteins having an amino acid sequence encoded by an open reading frame (ORF) of a TIMP gene, including the full length TIMP protein and fragments thereof, such as biologically active fragments and/or fragments corresponding to functional domains; and including fusions of the subject polypeptides to other proteins or parts thereof. Fragments of interest may vary in length, and in some instances are 10 aa or longer, such as 50 aa or longer, and including 100 aa or longer, and in some instances do not exceed 150 aa in length, where a given fragment will have a stretch of amino acids that is substantially the same as or identical to a subsequence found in any of SEQ ID NOS:1 to 4; where the subsequence may vary in length and in some instances is 10 aa or longer, such as 15 aa or longer, up to 50 aa or even longer.

In some instances, TIMP polypeptides employed in methods of invention include or more modifications. Modifications that may be present may vary, and include but are not limited to: amide bond substitutions, amino acid substitutions, including of cysteine residues/analogues, cyclization, pegylation, etc. Examples of modifications that may be found in TIMP polypeptides employed in methods of the invention are now reviewed in greater detail.

In some cases, TIMP polypeptides include one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of a TIMP polypeptide can be substituted. In another example, one or more amide linkages (—CO—NH—) in a TIMP polypeptide can be replaced with a linkage which is an isostere of an amide linkage, such as —CH$_2$NH—, —CH$_2$S—, —CH$_2$CH$_2$—, —CH═CH-(cis and trans), —COCH$_2$—, —CH(OH)CH$_2$— or —CH$_2$SO—. One or more amide linkages in a TIMP polypeptide can also be replaced by, for example, a reduced isostere pseudopeptide bond.

One or more amino acid substitutions can be made in a TIMP polypeptide. The following are non-limiting examples: a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions; b) substitution of aromatic-substituted hydrophobic amino acids, including phenylalanine, tryptophan, tyrosine, sulfo-tyrosine, biphenylalanine, 1-naphthylalanine, 2-naphthyl-alanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenyl-alanine, 2'-, 3'-, or 4'-methyl-, 2-, 3- or 4-biphenylalanine, and 2- or 3-pyridylalanine; c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2, 3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid; d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids; e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, a TIMP polypeptide includes one or more naturally occurring non-genetically encoded L-amino acids, synthetic L-amino acids, or D-enantiomers of an amino acid. For example, a TIMP polypeptide can include only D-amino acids. For example, a TIMP polypeptide can include one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

A cysteine residue or a cysteine analog can be introduced into a TIMP polypeptide to provide for linkage to another peptide via a disulfide linkage or to provide for cyclization of the TIMP polypeptide. a TIMP polypeptide can be cyclized. One or more cysteines or cysteine analogs can be introduced into a TIMP polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —(CH$_2$)$_n$—CO— or —(CH$_2$)$_n$—C$_6$H$_4$—CO—) with functional groups which allow for the introduction of a bridge. Some examples are disulfides, disulfide mimetics such as the —(CH$_2$)$_n$— carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

Modifications may be present that provide for improvements in one or more physical properties of the TIMP polypeptide. Improvements of physical properties include, for example, modulating immunogenicity; methods of increasing water solubility, bioavailability, serum half-life, and/or therapeutic half-life; and/or modulating biological activity. Examples of such modifications include, but are not limited to: pegylation, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation:

The clinical effectiveness of protein therapeutics may be limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity. In addition to the beneficial effects of pegylation on pharmacokinetic parameters, pegylation itself may enhance activity. PEGs suitable for conjugation to a polypeptide sequence are generally soluble in water at room temperature, and have the general formula R(O—CH$_2$—CH$_2$)$_n$O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa. Pegylated TIMP polypeptides may be conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by any convenient reaction conditions and purification. Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies, such as those known in the art, can be applied herein. PEG may be bound to a polypeptide of the present disclosure via a terminal reactive group (a "spacer") which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine. Conjugation of one or more of the polypeptide sequences to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest. This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present. Glycosylation can dramatically affect the physical properties (e.g., solubility) of polypeptides such as TIMP polypeptides and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide. Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants. The polypeptide sequences of the present disclosure may optionally be altered through changes at the nucleic acid level, particularly by mutating the nucleic acid encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases. Dihydrofolate reductase (DHFR)-deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

In some embodiments, the polypeptides are non-naturally glycosylated. By non-naturally glycosylated is meant that the polypeptide has a glycosylation pattern, if present, which is not the same as the glycosylation pattern found in the corresponding naturally occurring protein. For example, a human TIMP2 employed in methods of the invention of this particular embodiment is characterized by having a glycosylation pattern, if glycosylated at all, that differs from that of naturally occurring human TIMP2. Thus, the non-naturally glycosylated TIMP polypeptides of this embodiment include non-glycosylated TIMP polypeptides, i.e. proteins having no covalently bound glycosyl groups.

Polysialylation:

The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of in vivo activity, and reduction in immunogenicity and antigenicity (see, e.g., G. Gregoriadis et al., Int. J. Pharmaceutics 300(1-2):125-30). As with modifications with other conjugates (e.g., PEG), various techniques for site-specific polysialylation are available (see, e.g., T. Lindhout et al., (2011) PNAS 108(18)7397-7402).

Albumin Fusion:

Additional suitable components and molecules for conjugation include albumins such as human serum albumin (HSA), cyno serum albumin, and bovine serum albumin (BSA). Mature HSA, a 585 amino acid polypeptide (~67 kDa) having a serum half-life of ~20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulphide bridges. The three primary drug binding regions of albumin are located on each of the three domains within sub-domains IB, IIA and IIIA. Albumin synthesis takes place in the liver, which produces the short-lived, primary product preproalbumin. Thus, the full-length HSA has a signal peptide of 18 amino acids (MKWVTFISLLFLFSSAYS; SEQ ID NO:5) followed by a pro-domain of 6 amino acids (RGVFRR; SEQ ID NO:6); this 24 amino acid residue peptide may be referred to as the pre-pro domain. HSA can be expressed and secreted using its endogenous signal peptide as a pre-pro-domain. Alternatively, HSA can be expressed and secreted using a IgK signal peptide fused to a mature construct. Preproalbumin is rapidly co-translationally cleaved in the endoplasmic reticulum lumen at its amino terminus to produce the stable, 609-amino acid precursor polypeptide, proalbumin. Proalbumin then passes to the Golgi apparatus, where it is converted to the 585 amino acid mature albumin by a furin-dependent amino-terminal cleavage. The primary amino acid sequences, structure, and function of albumins are highly conserved across species, as are the processes of albumin synthesis and secretion. Albumin serum proteins comparable to HSA are found in, for example, cynomolgus monkeys, cows, dogs, rabbits and rats. Of the non-human species, bovine serum albumin (BSA) is the most structurally similar to HSA (see, e.g., Kosa et al., November 2007 J Pharm Sci. 96(11):3117-24). The present disclosure contemplates the use of albumin from non-human species, including, but not limited to, those set forth above, in, for example, the drug development process. According to the present disclosure, albumin may be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701). In the HSA-TIMP conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof. Intracellular cleavage may be carried out enzymatically by, for example, furin or caspase. Cells express a low level of these endogenous enzymes, which are capable of cleaving a portion of the fusion molecules intracellularly; thus, some of the polypeptides are secreted from the cell without being conjugated to HSA, while some of the polypeptides are secreted in the form of fusion molecules that comprise HSA. Embodiments of the present disclosure contemplate the use of various furin fusion constructs. For example, constructs may be designed that comprise the sequence RGRR, RKRKKR, RKKR, or RRRKKR. The present disclosure also contemplates extracellular cleavage (i.e., ex-vivo cleavage) whereby the fusion molecules are secreted from the cell, subjected to purification, and then cleaved. It is understood that the excision may dissociate the entire HSA-linker complex from the mature TIMP polypeptide, or less that the entire HSA-linker complex. As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake through the cell membrane, incorporation and expression of exogenous genetic material (exogenous nucleic acid). Transformation occurs naturally in some species of bacteria, but it can also be effected by artificial means in other cells. Furthermore, albumin itself may be modified to extend its circulating half-life. Fusion of the modified albumin to a TIMP polypeptide can be attained by the genetic manipulation techniques described above or by chemical conjugation; the resulting fusion molecule has a half-life that exceeds that of fusions with non-modified albumin. TIMP2-albumin fusion proteins of interest include those described in U.S. Pat. No. 7,163,805, the disclosure of which is herein incorporated by reference.

Several albumin-binding strategies have been developed as alternatives to direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog. The present disclosure also contemplates fusion proteins which comprise an albumin binding domain (ABD) polypeptide sequence and the sequence of one or more of the polypeptides described herein. Any ABD polypeptide sequence described in the literature can be a component of the fusion proteins. The components of the fusion proteins can be optionally covalently bonded through a linker, such as those linkers described herein. In some of the embodiments of the present disclosure, the fusion proteins comprise the ABD polypeptide sequence as an N-terminal moiety and the polypeptides described herein as a C-terminal moiety. The present disclosure also contemplates fusion proteins comprising a fragment of an albumin binding polypeptide, which fragment substantially retains albumin binding; or a multimer of albumin binding polypeptides or their fragments comprising at least two albumin binding polypeptides or their fragments as monomer units.

Conjugation with Other Molecules:

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing. Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule. A conjugate modification may result in a polypeptide sequence that retains activity with an additional or complementary function or activity derived from the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disease, disorder or condition as set forth herein (e.g., cancer). A TIMP polypeptide may also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide of the present disclosure. Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes. Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications:

The present disclosure contemplates the use of other modifications, currently known or developed in the future, of TIMP polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the polypeptide sequences' characteristics.

Linkers:

Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Exemplary flexible linkers include glycine polymers (G)n, glycine-serine polymers (for example, $(GS)_n$, $GSGGS_n$ (SEQ ID NO: 7), $GGGS_n$ (SEQ ID NO: 8), $(G_mS_o)_n$, $(G_mS_oG_m)_n$, $(G_mS_oG_mS_oG_m)_n$ (SEQ ID NO: 9)$_n$, $(GSGGS_m)_n$ (SEQ ID NO: 10)$_n$, $(GSGS_mG)_n$ (SEQ ID NO: 11)$_n$ and $(GGGS_m)_n$ (SEQ ID NO: 12)$_n$, and combinations thereof, where m, and o are each independently selected from an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO: 13), GGSGG (SEQ ID NO: 14), GSGSG (SEQ ID NO: 15), GSGGG (SEQ ID NO: 16), GGGSG (SEQ ID NO: 17), and GSSSG (SEQ ID NO: 18).

In some instances, systemic TIMP polypeptide levels is increased by administering a nucleic acid coding sequence to the subject under conditions sufficient for the coding sequence to be expressed in the subject. Depending on the desired TIMP polypeptide, the nucleic acid coding sequence may vary. Nucleic acids of interest include those encoding the TIMP polypeptides provided above. Specific nucleic acids of interest include, but are not limited to: Human TIMP2 (NCBI Reference Sequence: NM_003255.4); Human TIMP1 (NCBI Reference Sequence: NM_003254.2); Human TIMP3 (NCBI Reference Sequence: NM_000362.4) and Human TIMP4 (NCBI Reference Sequence: NM_003256.3).

By nucleic acid composition is meant a composition comprising a sequence of DNA having an open reading frame that encodes a TIMP polypeptide of interest, i.e., a TIMP coding sequence, and is capable, under appropriate conditions, of being expressed as a TIMP polypeptide. Also encompassed in this term are nucleic acids that are homologous, substantially similar or identical to the specific nucleic acids described above. In addition to the above described specific nucleic acid compositions, also of interest are homologues of the above sequences. In certain embodiments, sequence similarity between homologues is 20% or higher, such as 25% or higher, and including 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence may be 18 nt long or longer, such as 30 nt long, and may extend to the complete sequence that is being compared. Algorithms for sequence analysis are known in the art, such as BLAST, described in Altschul et al. (1990), J. Mol. Biol. 215:403-10 (using default settings, i.e. parameters w=4 and T=17). Of particular interest in certain embodiments are nucleic acids of substantially the same length as specific human TIMP1 to TIMP4 nucleic acids mentioned above, where by substantially the same length is meant that any difference in length does not exceed about 20 number %, usually does not exceed about 10 number and more usually does not exceed about 5 number %; and have sequence identity to any of these sequences of at 90% or greater, such as 95% or greater and including 99% or greater over the entire length of the nucleic acid. In some embodiments, the nucleic acids have a sequence that is substantially similar or identical to the above specific sequences. By substantially similar is meant that sequence identity is 60% or greater, such as 75% or greater and including 80, 85, 90, or even 95% or greater. Nucleic acids of interest also include nucleic acids that encode the proteins encoded by the above described nucleic acids, but differ in sequence from the above described nucleic acids due to the degeneracy of the genetic code.

Nucleic acids as described herein may be present in a vector. Various vectors (e.g., viral vectors, bacterial vectors, or vectors capable of replication in eukaryotic and prokaryotic hosts) can be used in accordance with the present invention. Numerous vectors which can replicate in eukaryotic and prokaryotic hosts are known in the art and are commercially available. In some instances, such vectors used in accordance with the invention are composed of a bacterial origin of replication and a eukaryotic promoter operably linked to a DNA of interest.

Viral vectors used in accordance with the invention may be composed of a viral particle derived from a naturally-occurring virus which has been genetically altered to render the virus replication-defective and to express a recombinant gene of interest in accordance with the invention. Once the virus delivers its genetic material to a cell, it does not generate additional infectious virus but does introduce exogenous recombinant genes into the cell, preferably into the genome of the cell. Numerous viral vectors are well known in the art, including, for example, retrovirus, adenovirus, adeno-associated virus, herpes simplex virus (HSV), cytomegalovirus (CMV), vaccinia and poliovirus vectors.

The DNA of interest may be administered using a non-viral vector, for example, as a DNA- or RNA-liposome complex formulation. Such complexes comprise a mixture of lipids which bind to genetic material (DNA or RNA), providing a hydrophobic coat which allows the genetic material to be delivered into cells. Liposomes which can be used in accordance with the invention include DOPE (dioleyl phosphatidyl ethanol amine), CUDMEDA (N-(5-cholestrum-3-.beta.-ol 3-urethanyl)-N',N'-dimethylethylene diamine). When the DNA of interest is introduced using a liposome, in some instances one first determines in vitro the optimal values for the DNA: lipid ratios and the absolute concentrations of DNA and lipid as a function of cell death and transformation efficiency for the particular type of cell to be transformed. These values can then be used in or extrapolated for use in in vivo transformation. The in vitro determinations of these values can be readily carried out using techniques which are well known in the art.

Other non-viral vectors may also be used in accordance with the present invention. These include chemical formulations of DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids to allow coupling of the nucleic acid compounds to a carrier molecule such as a protein or lipid, or derivative thereof. Exemplary protein carrier molecules include antibodies specific to the cells of a targeted secretory gland or receptor ligands, i.e., molecules capable of interacting with receptors associated with a cell of a targeted secretory gland.

DNA constructs may include a promoter to facilitate expression of the DNA of interest within a target cell, such as a strong, eukaryotic promoter. Exemplary eukaryotic promoters include promoters from cytomegalovirus (CMV), mouse mammary tumor virus (MMTV), Rous sarcoma virus (RSV), and adenovirus. More specifically, exemplary promoters include the promoter from the immediate early gene of human CMV (Boshart et al., Cell 41:521-530, 1985) and the promoter from the long terminal repeat (LTR) of RSV (Gorman et al., Proc. Natl. Acad. Sci. USA 79:6777-6781, 1982).

Instead of administration of a TIMP polypeptide, e.g., as described above, the level of systemic TIMP active agent in the subject may be enhanced by stimulating endogenous production and/or release of a TIMP polypeptide in vivo.

Also of interest are potentiators of TIMP activity. By TIMP potentiator is meant an agent or combination of agents that work to increase the desirable TIMP activity of endogenous TIMP polypeptides present in the subject being treated. The magnitude of the increase may vary, where in some instances the magnitude of the increase is 2-fold or greater, such as 5-fold or greater, including 10-fold or greater, e.g., 15-fold or greater, 20-fold or greater, 25-fold or greater (as compared to a suitable control). TIMP potentiators of interest may work through a variety of different mechanisms, e.g., by enhancing the binding interaction between a TIMP polypeptide and a desired target; by increasing the bioavailability of the endogenous pool, e.g., by sequestering undesirable competitive binding targets, etc.

In yet other embodiments, the agent is a small molecule agent that exhibits the desired TIMP activity. Naturally occurring or synthetic small molecule compounds of interest include numerous chemical classes, such as organic molecules, e.g., small organic compounds having a molecular weight of more than 50 and less than about 2,500 Daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In practicing methods of the invention, the active agent(s) may be administered to the adult mammal using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al., Anal Biochem. (1992) 205:365-368. The DNA may be coated onto gold microparticles, and delivered intradermally by a particle bombardment device, or "gene gun" as described in the literature (see, for example, Tang et al., Nature (1992) 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

In those embodiments where an effective amount of an active agent is administered to the adult mammal, the amount or dosage is effective when administered for a suitable period of time, such as one week or longer, including two weeks or longer, such as 3 weeks or longer, 4 weeks or longer, 8 weeks or longer, etc., so as to evidence a reduction in the impairment, e.g., cognition decline and/or cognitive improvement in the adult mammal. For example, an effective dose is the dose that, when administered for a suitable period of time, such as at least about one week, and maybe about two weeks, or more, up to a period of about 3 weeks, 4 weeks, 8 weeks, or longer, will slow e.g., by about 20% or more, e.g., by 30% or more, by 40% or more, or by 50% or more, in some instances by 60% or more, by 70% or more, by 80% or more, or by 90% or more, e.g., will halt, cognitive decline in a patient suffering from natural aging or an aging-associated disorder. In some instances, an effective amount or dose of active agent will not only slow or halt the progression of the disease condition but will also induce the reversal of the condition, i.e., will cause an improvement in cognitive ability. For example, in some instances, an effective amount is the amount that when administered for a suitable period of time, usually at least about one week, and maybe about two weeks, or more, up to a period of about 3 weeks, 4 weeks, 8 weeks, or longer will improve the cognitive abilities of an individual suffering from an aging-associated cognitive impairment by, for example 1.5-fold, 2-fold, 3-fold, 4-fold, 5-fold, in some instances 6-fold, 7-fold, 8-fold, 9-fold, or 10-fold or more relative to cognition prior to administration of the blood product.

Where desired, effectiveness of treatment may be assessed using any convenient protocol. Cognition tests and IQ test for measuring cognitive ability, e.g., attention and concentration, the ability to learn complex tasks and concepts, memory, information processing, visuospatial function, the ability to produce and understanding language, the ability to solve problems and make decisions, and the ability to perform executive functions, are well known in the art, any of which may be used to measure the cognitive ability of the individual before and/or during and after treatment with the subject blood product, e.g., to confirm that an effective amount has been administered. These include, for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, the Alzheimer's Disease Assessment Scale (ADAS-Cog), the Psychogeriatric Assessment Scale (PAS) and the like. Progression of functional brain improvements may be detected by brain imaging techniques, such as Magnetic Resonance Imaging (MRI) or Positron Emission Tomography (PET) and the like. A wide range of additional functional assessments may be applied to monitor activities of daily living, executive functions, mobility, etc. In some embodiments, the method comprises the step of measuring cognitive ability, and detecting a decreased rate of cognitive decline, a stabilization of cognitive ability, and/or an increase in cognitive ability after administration of the blood product as compared to the cognitive ability of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, the reduction in synaptic plasticity and loss of synapses that occurs during the natural aging process or during the progression of an aging-associated disorder. In other words, cells present in adult mammals treated in accordance with methods of the invention will become more responsive to cues, e.g., activity cues, which promote the formation and maintenance of synapses.

Performance of methods of the invention, e.g., as described above, may manifest as improvements in observed synaptic plasticity, both in vitro and in vivo as an induction of long term potentiation. For example, the induction of LTP in neural circuits may be observed in awake individuals, e.g., by performing non-invasive stimulation techniques on awake individuals to induce LTP-like long-lasting changes in localized neural activity (Cooke S F, Bliss TV (2006) Plasticity in the human central nervous system. Brain. 129(Pt 7):1659-73); mapping plasticity and increased neural circuit activity in individuals, e.g., by using positron emission tomography, functional magnetic resonance imaging, and/or transcranial magnetic stimulation (Cramer and Bastings, "Mapping clinically relevant plasticity after stroke," Neuropharmacology (2000)39:842-51); and by detecting neural plasticity following learning, i.e., improvements in memory, e.g., by assaying retrieval-related brain activity (Buchmann et al., "Prion protein M129V polymorphism affects retrieval-related brain activity," Neuropsychologia. (2008) 46:2389-402) or, e.g., by imaging brain tissue by functional magnetic resonance imaging (fMRI) following repetition priming with familiar and unfamiliar objects (Soldan et al., "Global familiarity of visual stimuli affects repetition-related neural plasticity but not repetition priming," Neuroimage. (2008) 39:515-26; Soldan et al., "Aging does not affect brain patterns of repetition effects associated with perceptual priming of novel objects," J. Cogn. Neurosci. (2008) 20:1762-76). In some embodiments, the method includes the step of measuring synaptic plasticity, and detecting a decreased rate of loss of synaptic plasticity, a stabilization of synaptic plasticity, and/or an increase in synaptic plasticity after administration of the blood product as compared to the synaptic plasticity of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

In some instances, the methods result in a change in expression levels of one or more genes in one or more tissues of the host, e.g., as compared to a suitable control (such as described in the Experimental section, below). The change in expression level of a given gene may be 0.5 fold or greater, such as 1.0 fold or greater, including 1.5 fold or greater. The tissue may vary, and in some instances is nervous system tissue, e.g., central nervous system tissue, including brain tissue, e.g., hippocampal tissue. In some instances, the modulation of hippocampal gene expression is manifested as enhanced hippocampal plasticity, e.g., as compared to a suitable control. In some instances, the one or more genes whose expression is modulated, e.g., enhanced, is a gene encoding a product that is a member of a plasticity related signaling pathway (i.e., a synaptic plasticity regulation gene), e.g., Tlr4, Gria1, Kcnj10, Kdr, Ncam, Sdfr1, Egr1, Fos proteins, e.g., c-Fos, Drd1a, Stxbp1, Mef2c, Cntn2, Junb, Bdnf and CamK2a, etc. In some instances, the modulation of hippocampal gene expression is manifested as enhanced hippocampal plasticity, e.g., as compared to a suitable control. In some instances, the one or more genes whose expression is modulated, e.g., enhanced, is a gene encoding a product that is a member of network related to synaptic plasticity and learning and memory, such as but not limited to: RELN, NTRK3, EPHA4, etc.

In some instances, treatment results in an enhancement in the levels of one or more proteins in one or more tissues of the host, e.g., as compared to a suitable control (such as described in the Experimental section, below). The change in protein level of a given protein may be 0.5 fold or greater, such as 1.0 fold or greater, including 1.5 fold or greater, where in some instances the level may approach that of a healthy wild-type level, e.g., within 50% or less, such as 25% or less, including 10% or less, e.g., 5% or less of the healthy wild-type level. The tissue may vary, and in some instances is nervous system tissue, e.g., central nervous system tissue, including brain tissue, e.g., hippocampal tissue.

In some instances, the methods result in one or more structural changes in one or more tissues. The tissue may vary, and in some instances is nervous system tissue, e.g., central nervous system tissue, including brain tissue, e.g., hippocampal tissue. Structure changes of interest include an increase in dendritic spine density of mature neurons in the dentate gyrus (DG) of the hippocampus, e.g., as compared to a suitable control. In some instances, the modulation of hippocampal structure is manifested as enhanced synapse formation or function, e.g., as compared to a suitable control. In some instances, the methods may result in an enhancement of long term potentiation, e.g., as compared to a suitable control.

In some instances, practice of the methods, e.g., as described above, results in an increase in neurogenesis in the adult mammal. The increase may be identified in a number of different ways, e.g., as described below in the Experimental section. In some instances, the increase in neurogenesis manifests as an increase the amount of Dcx-positive immature neurons, e.g., where the increase may be 1.5-fold or greater. In some instances, the increase in neurogenesis manifests as an increase in the number of BrdU/NeuN positive cells, where the increase may be 1.5-fold or greater.

In some instances, the methods result in enhancement in learning and memory, e.g., as compared to a suitable control. Enhancement in learning and memory may be evaluated in a number of different ways, e.g., the contextual fear conditioning, Barnes maze, and/or radial arm water maze (RAWM) paradigms described in the experimental section, below. When measured by contextual fear conditioning, treatment results in some instances in increased freezing in contextual, but not cued, memory testing. When measured by Barnes maze, treatment results in some instances in enhanced learning and memory for escape hole location during the testing phase of the task on any day of the task. When measured by RAWM, treatment results in some instances in enhanced learning and memory for platform location during the testing phase of the task. In some instances, treatment is manifested as enhanced cognitive improvement in hippocampal-dependent learning and memory, e.g., as compared to a suitable control.

In some embodiments, the methods may be performed in conjunction with an active agent having activity suitable to treat aging-associated cognitive impairment. For example, a number of active agents have been shown to have some efficacy in treating the cognitive symptoms of Alzheimer's disease (e.g., memory loss, confusion, and problems with thinking and reasoning), e.g., cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some instances, the methods are practiced in conjunction with one or more additional non-TIMP polypeptides active agents, where such non-TIMP polypeptide active agent exhibit a desirable anti-aging associated condition activity, e.g., as described above. Examples of such non-TIMP polypeptide active agents include, but are not limited to: chemokine (C—C motif) ligand 2 (CCL2) (i.e., MCP1) and C—C motif chemokine 11 (i.e., chemotactic protein or eotaxin-1) and agonists/mimetics thereof (e.g., as described in published application no. 20130040844, the disclosure of which is herein incorporated by reference0; Granulocyte-macrophage colony-stimulating factor (GM-CSF)(i.e., colony stimulating factor 2 or CSF2); etc. In such instances, the active agent may be any type of convenient active agent, including those types of agents discussed above in connection with TIMP active agents, e.g., polypeptides and mimetics/fragments thereof, small molecules, nucleic acids, potentiators, etc.

In some aspects of the subject methods, the method further comprises the step of measuring cognition and/or synaptic plasticity after treatment, e.g., using the methods described herein or known in the art, and determining that the rate of cognitive decline or loss of synaptic plasticity have been reduced and/or that cognitive ability or synaptic plasticity have improved in the individual. In some such instances, the determination is made by comparing the results of the cognition or synaptic plasticity test to the results of the test performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having a cognitive impairment, e.g., using the methods described herein or known in the art for measuring cognition and synaptic plasticity, prior to administering the subject plasma-comprising blood product. In some instances, the diagnosing will comprise measuring cognition and/or synaptic plasticity and comparing the results of the cognition or synaptic plasticity test to one or more references, e.g., a positive control and/or a negative control. For example, the reference may be the result(s) of the test performed by one or more age-matched individuals that experience aging-associated cognitive impairments (i.e., positive controls) or that do not experience aging-associated cognitive impairments (i.e., negative controls). As another example, the reference may be the result(s) of the test performed by the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having an aging-associated disorder, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, muscular dystrophy, dementia, and the like. Methods for diagnosing such aging-associated disorders are well-known in the art, any of which may be used by the ordinarily skilled artisan in diagnosing the individual. In some embodiments, the subject methods further comprise both diagnosing an individual as having an aging-associated disorder and as having a cognitive impairment.

Utility

The subject methods find use in treating, including preventing, aging-associated impairments and conditions associated therewith, such as impairments in the cognitive ability of individuals. Individuals suffering from or at risk of developing an aging-associated cognitive impairments include individuals that are about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

Mild Cognitive Impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

Alzheimer's Disease (AD).

Alzheimer's disease is a progressive, inexorable loss of cognitive function associated with an excessive number of senile plaques in the cerebral cortex and subcortical gray matter, which also contains β-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease.

Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function.

In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Frontotemporal Dementia.

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected: Behavioural variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies". Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's Disease.

Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic Lateral Sclerosis.

Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years. Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis.

Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma.

Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

Myotonic Dystrophy.

Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia.

Dementia describes class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall. Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (PDD) would be the diagnosis when dementia onset is more than a year after the onset of Parkinson's. DLB is diagnosed when cognitive symptoms begin at the same time or within a year of Parkinson symptoms.

Progressive Supranuclear Palsy.

Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorders long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

Ataxia.

People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-System Atrophy.

Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation. The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

In some embodiments, the subject methods and compositions find use in slowing the progression of aging-associated cognitive impairment. In other words, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

Combination Therapies

Active agents of the invention can be administered to a subject alone or in combination with an additional, i.e., second, active agent. As such, in some cases, the subject method further comprises administering to the subject at least one additional compound. Any convenient agents may be utilized. For example, TIMP active agents can be supplied alone or in conjunction with one or more other drugs, such as drugs employed in the treatment of aging associated conditions, e.g., cholinesterase inhibitors (e.g., Donepezil, Rivastigmine, Galantamine, Tacrine), Memantine, Vitamin E, citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon); non-TIMP polypeptide active agents; e.g., chemokine (C—C motif) ligand 2 (CCL2) (i.e., MCP1); C—C motif chemokine 11 (i.e., chemotactic protein or eotaxin-1); Granulocyte-macrophage colony-stimulating factor (GM-CSF)(i.e., colony stimulating factor 2 or CSF2); etc.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug with a pharmaceutical composition of the present invention means administration of the drug and nucleoside agent at such time that both the known drug and the composition of the present invention will have a therapeutic effect. Such concomitant administration may involve concurrent (i.e. at the same time), prior, or subsequent administration of the drug with respect to the administration of a subject nucleoside agent. Routes of administration of the two agents may vary, where representative routes of administration are described in greater detail below. A person of ordinary skill in the art would have no difficulty determining the appropriate timing, sequence and dosages of administration for particular drugs and nucleoside agents of the present invention.

In some embodiments, the compounds are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Pharmaceutical Preparations

Also provided are pharmaceutical preparations of the subject compounds. The subject compounds can be incorporated into a variety of formulations for administration to a subject. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous cyclodextrin solution further comprise dextrose, e.g., about 5% dextrose.

Dosage levels of the order of from about 0.01 mg to about 140 mg/kg of body weight per day are useful in representative embodiments, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host.

Kits & Systems

Also provided are kits and systems that find use in practicing embodiments of the methods, such as those described as described above. The term "system" as employed herein refers to a collection of two or more different active agents, present in a single composition or in disparate compositions, that are brought together for the purpose of practicing the subject methods. The term "kit" refers to a packaged active agent or agents. For example, kits and systems for practicing the subject methods may include one or more pharmaceutical formulations. As such, in certain embodiments the kits may include a single pharmaceutical composition, present as one or more unit dosages, where the composition may include one or more expression/activity inhibitor compounds. In yet other embodiments, the kits may include two or more separate pharmaceutical compositions, each containing a different active compound.

Also of interest are kits and systems finding use in assays of the invention, e.g., as described above. Such kits and systems may include one or more components of the assays, e.g., vectors encoding fusion proteins, enzyme substrates, buffers, etc.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

The following examples are provided by way of illustration and not by way of limitation.

EXPERIMENTAL

Recombinant TIMP2 protein was delivered at a concentration of 50 µg/kg four times over the course of a week by intraperitoneal injection in aged wildtype (C57Bl/6J) mice. Brains of treated mice revealed elevated levels of active neurons, namely those expressing the immediate early gene c-Fos in the dentate gyrus subregion of the hippocampus. Eight (long-term) intraperitoneal injections (50 µg/kg) of TIMP2 were given to aged wildtype mice every other day prior to Barnes maze, nesting, and fear conditioning assessment. Behavioral testing revealed significantly improved performance in all three tasks in TIMP2-treated mice. Seven (long-term) intraperitoneal injections (50 µg/kg) of TIMP2 were given to aged wildtype mice every other day alone or in combination with another cognition-promoting factor, CSF2. Brains of TIMP2 and TIMP2+CSF2 mice revealed significantly elevated levels of c-Fos+(active) neurons in the dentate gyrus.

The results demonstrated that TIMP2 was sufficient to elevate the number of c-Fos-expressing cells in the hippocampus of aged mice. When administered systemically over a longer timecourse, TIMP2 is sufficient to increase the number of c-Fos-expressing cells, reverse learning and memory deficits in several behavioral paradigms, and restore impairments in nesting ability. The above results demonstrate that TIMP2 is suitable to provide cognitive (learning and memory) benefits to patients suffering from age-related cognitive impairments or neurodegenerative diseases that decrease synaptic function, e.g. Alzheimer's disease. Our discovery represents the first description of a protein (TIMP2) that declines with age in blood that could be used to reverse impairments in synaptic plasticity and age-related learning and memory deficits. TIMP2, when administered systemically for a period of only ~2 weeks, is able to confer enhanced plasticity and memory and learning function without the need for direct to delivery to the brain.

Figure 1B:
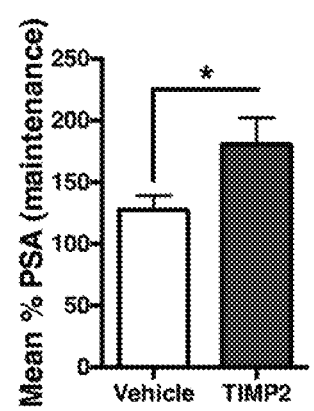
FIG. 1B provides quantification of the maintenance phase of the PSA shown in FIG. 1A.

Systemic TIMP2 treatment in aged mice robustly improves long-term potentiation, a cellular correlate of learning and memory. Brain slices isolated from aged wildtype mice that were treated with recombinant TIMP2 (i.p., 50 µg/kg) display enhanced long-term potentiation (LTP) as compared to a control (vehicle). Shown in FIG. 1A are population spike amplitudes (PSA) within dentate gyrus following stimulation in the perforant path of the hippocampus. Quantification of the maintenance phase of the PSA shown in FIG. 1A is provided in FIG. 1B. (Mean+/−SEM; Student's t test; *$P<0.05$.)

Figure 2:
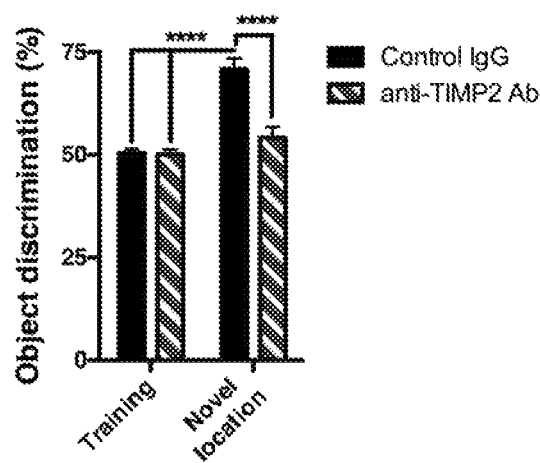
FIG. 2 shows the results of anti-TIMP2 antibody treatment on object discrimination.

Systemic TIMP2 is necessary for hippocampal-dependent spatial memory, as assessed in a novel location recognition task. TIMP2 levels in young wildtype mice were targeted for approximately one month using an antibody-mediated neutralization approach (60 µg/kg) prior to assessment of object location displacement discrimination 24 hours after training. (Mean+/−SEM; 2-way ANOVA, followed by Tukey's post hoc test; ****$P<0.0001$.) The results are shown in FIG. 2.

There are currently no effective treatments for the significant decline in synaptic plasticity, learning/memory, and other cognitive ability associated with normal brain aging or neurodegeneration. We have identified a youth-derived protein, TIMP2, with strong rejuvenating activity. TIMP2, when administered systemically for a relatively short course of treatment, is able to confer enhanced plasticity and memory and learning function without the need for direct delivery to the brain. TIMP2 is not a growth factor, nor is it a canonical immune signaling molecule, which highlights an additional advantage, namely that TIMP2 affords the ability to target brain aging processes without supplying a potentially tumorigenic or proinflammatory molecule that may harm other organ systems. Moreover, utilizing a protein naturally produced and found in blood to limit cognitive dysfunction is unlikely to produce harmful side effects compared to conventional small molecule drug design.

No effective therapeutic agents exist to treat the age-related outcomes of CNS aging. Our approach allows for facile, systemic treatment of elderly patients or those otherwise suffering from cognitive impairment with TIMP2, a protein normally produced by the body.

Notwithstanding the appended clauses, the disclosure is also defined by the following clauses:

1. A method of treating an adult mammal for an aging-associated condition, the method comprising:
enhancing a TIMP activity in the mammal in a manner sufficient to treat the adult mammal for the aging-associated condition.

2. The method according to Clause 1, wherein the TIMP activity is a TIMP1, TIMP2, TIMP3 or TIMP4 activity.
3. The method according to Clause 2, wherein the TIMP activity is a TIMP2 activity.
4. The method according to any of Clauses 1 to 3, where the method comprises enhancing a systemic TIMP activity.
5. The method according to any of Clauses 1 to 4, wherein the method comprises increasing a systemic level of a TIMP active agent in the mammal.
6. The method according to Clause 5, wherein the systemic level of a TIMP active agent is increased by administering a TIMP active agent to the mammal.
7. The method according to Clause 6, wherein the TIMP active agent is a TIMP polypeptide or mimetic thereof.
8. The method according to Clause 7, wherein the TIMP active agent is a TIMP polypeptide.
9. The method according to Clause 8, wherein the TIMP polypeptide has a sequence that is at least 60% identical to any of SEQ ID NOS: 1 to 4.
10. The method according to any of clauses 1 to 5, wherein the method comprises enhancing expression of an endogenous TIMP coding sequence.
11. The method according to Clauses 1 to 4, wherein the method comprises potentiating TIMP in the subject.
12. The method according to any of the preceding clauses, wherein the mammal is a primate.
13. The method according to Clause 12, wherein the primate is a human.
14. The method according to any of the preceding clauses, wherein the adult mammal is an elderly mammal.
15. The method according to Clause 14, wherein the elderly mammal is a human that is 60 years or older.
16. The method according to any of the preceding clauses, wherein the aging-associated condition comprises a cognitive impairment.
17. The method according to any of the preceding clauses, wherein the adult mammal suffers from an aging associated disease condition.
18. The method according to any of the preceding clauses, wherein the aging associated disease condition is a cognitive decline disease condition.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of ameliorating a symptom of aging-associated cognitive impairment or decline in an adult mammal, the method comprising:
administering a Tissue inhibitor of metalloproteinase (TIMP) polypeptide or a nucleic acid encoding a TIMP polypeptide to the mammal, thereby enhancing a TIMP activity in the mammal in a manner sufficient to ameliorate a symptom of aging-associated cognitive impairment or decline.

2. The method according to claim 1, wherein the TIMP polypeptide is a TIMP1 polypeptide.

3. The method according to claim 1, wherein the TIMP polypeptide is a TIMP2 polypeptide.

4. The method according to claim 1, where the method comprises enhancing a systemic TIMP activity.

5. The method according to claim 1, wherein the method comprises increasing a systemic level of a TIMP polypeptide in the mammal.

6. The method according to claim 1 wherein the TIMP polypeptide has a sequence that is at least 90% identical to any of SEQ ID NOS: 1 to 4.

7. The method according to claim 1, wherein the mammal is a primate.

8. The method according to claim 7, wherein the primate is a human.

9. The method according to claim 1, wherein the adult mammal is an elderly mammal.

10. The method according to claim 1, comprising administering to the subject a pegylated TIMP polypeptide.

11. The method according to claim 1, comprising administering to the subject a TIMP polypeptide fused to an Fc region of an antibody.

12. The method according to claim 11, wherein the antibody is an IgG antibody.

13. The method according to claim 1, wherein the TIMP polypeptide is a TIMP3 polypeptide.

14. The method according to claim 1, wherein the TIMP polypeptide is a TIMP4 polypeptide.

15. The method according to claim 1, comprising administering to the subject a nucleic acid encoding the TIMP polypeptide.

16. The method according to claim 15, comprising administering to the subject a nucleic acid encoding the TIMP1 polypeptide.

17. The method according to claim 15, comprising administering to the subject a nucleic acid encoding the TIMP2 polypeptide.

18. The method according to claim 15, comprising administering to the subject a nucleic acid encoding the TIMP3 polypeptide.

19. The method according to claim 15, comprising administering to the subject a nucleic acid encoding the TIMP4 polypeptide.

* * * * *

```
                      SEQUENCE LISTING

<160> NUMBER OF SEQ ID NOS: 22

<210> SEQ ID NO 1
<211> LENGTH: 220
<212> TYPE: PRT
<213> ORGANISM: Homo sapiens

<400> SEQUENCE: 1

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
    50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Thr Gln Lys Lys Ser Leu
    130                 135                 140

Asn His Arg Tyr Gln Met Gly Cys Glu Cys Lys Ile Thr Arg Cys Pro
```

```
              145                 150                 155                 160
Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
        195                 200                 205

Pro Pro Lys Gln Glu Phe Leu Asp Ile Glu Asp Pro
    210                 215                 220

<210> SEQ ID NO 2
<211> LENGTH: 207
<212> TYPE: PRT
<213> ORGANISM: Homo sapiens

<400> SEQUENCE: 2

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 3
<211> LENGTH: 211
<212> TYPE: PRT
<213> ORGANISM: Homo sapiens

<400> SEQUENCE: 3

Met Thr Pro Trp Leu Gly Leu Ile Val Leu Leu Gly Ser Trp Ser Leu
1               5                   10                  15

Gly Asp Trp Gly Ala Glu Ala Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
```

```
                50                  55                  60
Lys Gln Met Lys Met Tyr Arg Gly Phe Thr Lys Met Pro His Val Gln
 65                  70                  75                  80

Tyr Ile His Thr Glu Ala Ser Glu Ser Leu Cys Gly Leu Lys Leu Glu
                 85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210

<210> SEQ ID NO 4
<211> LENGTH: 224
<212> TYPE: PRT
<213> ORGANISM: Homo sapiens

<400> SEQUENCE: 4

Met Pro Gly Ser Pro Arg Pro Ala Pro Ser Trp Val Leu Leu Leu Arg
 1               5                  10                  15

Leu Leu Ala Leu Leu Arg Pro Pro Gly Leu Gly Glu Ala Cys Ser Cys
                20                  25                  30

Ala Pro Ala His Pro Gln Gln His Ile Cys His Ser Ala Leu Val Ile
             35                  40                  45

Arg Ala Lys Ile Ser Ser Glu Lys Val Val Pro Ala Ser Ala Asp Pro
 50                  55                  60

Ala Asp Thr Glu Lys Met Leu Arg Tyr Glu Ile Lys Gln Ile Lys Met
 65                  70                  75                  80

Phe Lys Gly Phe Glu Lys Val Lys Asp Val Gln Tyr Ile Tyr Thr Pro
                 85                  90                  95

Phe Asp Ser Ser Leu Cys Gly Val Lys Leu Glu Ala Asn Ser Gln Lys
            100                 105                 110

Gln Tyr Leu Leu Thr Gly Gln Val Leu Ser Asp Gly Lys Val Phe Ile
        115                 120                 125

His Leu Cys Asn Tyr Ile Glu Pro Trp Glu Asp Leu Ser Leu Val Gln
130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175

Leu Trp Thr Asp Trp Leu Leu Glu Arg Lys Leu Tyr Gly Tyr Gln Ala
            180                 185                 190

Gln His Tyr Val Cys Met Lys His Val Asp Gly Thr Cys Ser Trp Tyr
        195                 200                 205
```

```
Arg Gly His Leu Pro Leu Arg Lys Glu Phe Val Asp Ile Val Gln Pro
    210                 215                 220
```

<210> SEQ ID NO 5
<211> LENGTH: 18
<212> TYPE: PRT
<213> ORGANISM: Homo sapiens

<400> SEQUENCE: 5

```
Met Lys Trp Val Thr Phe Ile Ser Leu Leu Phe Leu Phe Ser Ser Ala
1               5                   10                  15

Tyr Ser
```

<210> SEQ ID NO 6
<211> LENGTH: 6
<212> TYPE: PRT
<213> ORGANISM: Homo sapiens

<400> SEQUENCE: 6

```
Arg Gly Val Phe Arg Arg
1               5
```

<210> SEQ ID NO 7
<211> LENGTH: 5
<212> TYPE: PRT
<213> ORGANISM: Homo sapiens

<400> SEQUENCE: 7

```
Gly Ser Gly Gly Ser
1               5
```

<210> SEQ ID NO 8
<211> LENGTH: 4
<212> TYPE: PRT
<213> ORGANISM: Homo sapiens

<400> SEQUENCE: 8

```
Gly Gly Gly Ser
1
```

<210> SEQ ID NO 9
<211> LENGTH: 5
<212> TYPE: PRT
<213> ORGANISM: Homo sapiens

<400> SEQUENCE: 9

```
Gly Ser Gly Ser Gly
1               5
```

<210> SEQ ID NO 10
<211> LENGTH: 5
<212> TYPE: PRT
<213> ORGANISM: Homo sapiens

<400> SEQUENCE: 10

```
Gly Ser Gly Gly Ser
1               5
```

<210> SEQ ID NO 11
<211> LENGTH: 5
<212> TYPE: PRT
<213> ORGANISM: Homo sapiens

<400> SEQUENCE: 11

Gly Ser Gly Ser Gly
1               5

<210> SEQ ID NO 12
<211> LENGTH: 4
<212> TYPE: PRT
<213> ORGANISM: Homo sapiens

<400> SEQUENCE: 12

Gly Gly Gly Ser
1

<210> SEQ ID NO 13
<211> LENGTH: 4
<212> TYPE: PRT
<213> ORGANISM: Homo sapiens

<400> SEQUENCE: 13

Gly Gly Ser Gly
1

<210> SEQ ID NO 14
<211> LENGTH: 5
<212> TYPE: PRT
<213> ORGANISM: Homo sapiens

<400> SEQUENCE: 14

Gly Gly Ser Gly Gly
1               5

<210> SEQ ID NO 15
<211> LENGTH: 5
<212> TYPE: PRT
<213> ORGANISM: Homo sapiens

<400> SEQUENCE: 15

Gly Ser Gly Ser Gly
1               5

<210> SEQ ID NO 16
<211> LENGTH: 5
<212> TYPE: PRT
<213> ORGANISM: Homo sapiens

<400> SEQUENCE: 16

Gly Ser Gly Gly Gly
1               5

<210> SEQ ID NO 17
<211> LENGTH: 5
<212> TYPE: PRT
<213> ORGANISM: Homo sapiens

<400> SEQUENCE: 17

Gly Gly Gly Ser Gly
1               5

<210> SEQ ID NO 18
<211> LENGTH: 5
<212> TYPE: PRT
<213> ORGANISM: Homo sapiens

<400> SEQUENCE: 18

Gly Ser Ser Ser Gly
1               5

```
-continued

<210> SEQ ID NO 19
<211> LENGTH: 4
<212> TYPE: PRT
<213> ORGANISM: Homo sapiens

<400> SEQUENCE: 19

Arg Gly Arg Arg
1

<210> SEQ ID NO 20
<211> LENGTH: 6
<212> TYPE: PRT
<213> ORGANISM: Homo sapiens

<400> SEQUENCE: 20

Arg Lys Arg Lys Lys Arg
1               5

<210> SEQ ID NO 21
<211> LENGTH: 4
<212> TYPE: PRT
<213> ORGANISM: Homos sapiens

<400> SEQUENCE: 21

Arg Lys Lys Arg
1

<210> SEQ ID NO 22
<211> LENGTH: 6
<212> TYPE: PRT
<213> ORGANISM: Homo sapiens

<400> SEQUENCE: 22

Arg Arg Arg Lys Lys Arg
1               5
```